(12) United States Patent
Tanaka et al.

(10) Patent No.: US 11,324,466 B2
(45) Date of Patent: May 10, 2022

(54) CREATING MONOCHROMATIC CT IMAGE

(71) Applicant: National University Corporation Hokkaido University, Sapporo (JP)

(72) Inventors: Sodai Tanaka, Sapporo (JP); Hiroki Shirato, Sapporo (JP)

(73) Assignee: NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 93 days.

(21) Appl. No.: 15/931,292

(22) Filed: May 13, 2020

(65) Prior Publication Data

US 2020/0359980 A1    Nov. 19, 2020

(30) Foreign Application Priority Data

May 15, 2019  (JP) .............................. JP2019-092373

(51) Int. Cl.
*A61B 6/00* (2006.01)
*A61B 6/03* (2006.01)
(Continued)

(52) U.S. Cl.
CPC .............. *A61B 6/482* (2013.01); *A61B 6/032* (2013.01); *A61B 6/5205* (2013.01);
(Continued)

(58) Field of Classification Search
CPC ........... A61B 6/03; A61B 6/032; A61B 6/482; A61B 6/5205; A61B 6/5211; A61B 6/5252; A61B 6/5258; A61B 2090/392; A61B 5/055; A61B 5/06; A61B 5/064; A61B 5/07; A61B 5/415; A61B 5/418;
(Continued)

(56) References Cited

U.S. PATENT DOCUMENTS

2009/0147919 A1* 6/2009 Goto ...................... A61B 6/482
378/86
2009/0262997 A1* 10/2009 Zou ......................... A61B 6/583
382/131

(Continued)

FOREIGN PATENT DOCUMENTS

WO    WO 2014/034618 A1    3/2014

*Primary Examiner* — Irakli Kiknadze
(74) *Attorney, Agent, or Firm* — Nixon Peabody LLP (57) ABSTRACT

An image processor applies computation processing to a plurality of CT images formed by irradiation of radiation of a plurality of energy levels to acquire monochromatic CT images. The image processor acquires a first energy level CT image formed by irradiation of first energy level radiation and a second energy level CT image formed by irradiation of second energy level radiation, applies a plurality of weighted computations to the first and second energy level CT images to compute a plurality of monochromatic CT images as a result of the weighted computations, segments a surrounding region of a highly-absorbent material circumferentially into a plurality of regions of interest having a predetermined area and calculates a standard deviation of the surrounding region by using a mean value of image data of each region of interest, for each monochromatic CT image, and selects a monochromatic CT image with a small standard deviation.

8 Claims, 6 Drawing Sheets

(51) Int. Cl.
*G06T 7/11* (2017.01)
*H05G 1/64* (2006.01)

(52) U.S. Cl.
CPC .............. *A61B 6/5258* (2013.01); *G06T 7/11* (2017.01); *G06T 2207/10081* (2013.01); *G06T 2207/30004* (2013.01)

(58) Field of Classification Search
CPC ......... A61B 5/6835; A61B 6/037; A61B 6/12; A61B 6/4057; A61B 6/4258; A61B 6/4417; A61B 6/4423; A61B 6/583; A61B 8/0833; A61B 8/4245; A61B 6/481; A61B 6/4014; A61B 6/405; A61B 6/4085; A61B 6/4241; A61B 6/504; A61B 6/505; A61B 6/5241; A61B 6/5282; A61B 6/4021; G06T 2207/10081; G06T 2207/20221; G06T 2207/30004; G06T 5/002; G06T 5/50; G06T 7/11; G06T 11/005; G06T 11/003; G06T 2211/408; G06T 11/008; G06T 2211/424; G06T 2207/30008; G06T 2200/04; G06T 2207/10072; G06T 7/143; G06T 7/149; G06T 7/155; G01T 1/161; G01T 1/1663; G01T 1/24; G01T 1/366; A61N 2005/1061; A61N 5/1039; A61N 5/1049; A61N 5/1065; G01N 2223/206; G01N 2223/419; G01N 2223/6126; G01N 23/046; G16H 30/40; G16H 50/20

USPC ............................ 378/4, 5, 18, 19, 9.8, 98.8
See application file for complete search history.

(56) References Cited

U.S. PATENT DOCUMENTS

| | | | |
|---|---|---|---|
| 2010/0131885 A1* | 5/2010 | Licato | A61B 6/482 |
| | | | 715/781 |
| 2013/0287260 A1* | 10/2013 | Taguchi | G01N 23/046 |
| | | | 382/103 |
| 2015/0164456 A1 | 6/2015 | Takamatsu | |
| 2016/0171648 A1* | 6/2016 | Thibault | G01T 1/36 |
| | | | 378/5 |
| 2019/0167218 A1* | 6/2019 | Hsieh | A61B 6/405 |
| 2021/0110583 A1* | 4/2021 | Lee | A61B 6/469 |

\* cited by examiner

CREATING MONOCHROMATIC CT IMAGE

CROSS REFERENCE TO RELATED APPLICATION

This application claims priority to Japanese Patent Application No. 2019-092373 filed on May 15, 2019, which is incorporated herein by reference in its entirety including the specification, claims, drawings, and abstract.

TECHNICAL FIELD

The present disclosure relates to creation of a monochromatic computed tomography (CT) image, in which computation processing is applied to a plurality of CT images obtained by irradiation of radiation at a plurality of energy levels to form a monochromatic CT image.

BACKGROUND

Computed Tomography (CT) apparatuses have been widely used in radiation diagnosis and treatment. A CT apparatus irradiates a subject or a patient with X-rays to create a tomographic image (CT image) based on a projection image.

It is known that the image quality of CT images is degraded due to various artifacts. If a highly-absorbent material such as metal is present in a living body, for example, so-called metal (highly-absorbent material) artifacts occur. that is, the energy spectrum of the X-ray changes or the X-ray intensity is insufficient in a detector, failing to obtain an accurate projection image. The metal artifacts can be eliminated by applying weighted computation to CT images obtained at two different tube voltages to thereby form a virtual monochromatic CT image (hereinafter referred to simply as a monochromatic CT image). Therefore, a function to obtain a monochromatic CT image from two X-ray CT images is being introduced in commercial X-ray CT apparatuses (see WO 2014/034618).

To obtain a monochromatic CT image, it is necessary to apply weighted computation to two CT images with appropriate weights. In existing X-ray CT apparatuses, the weight is manually set for computation of the monochromatic CT image. Specifically, the operator visually judges the obtained monochromatic CT image while changing the weight, thereby selecting an appropriate weight. This requires the operator's judging ability and also takes time for the adjustment of weights.

SUMMARY

In accordance with an aspect, the disclosure provides a method for creating a monochromatic CT image by applying computation processing to a plurality of CT images formed by irradiation of radiation at a plurality of energy levels. The method includes acquiring a first energy level CT image by irradiation of radiation of a first energy level; acquiring a second energy level CT image by irradiation of radiation of a second energy level; applying a plurality of weighted computations to the first energy level CT image and the second energy level CT image that are acquired, to obtain a plurality of monochromatic CT images as a result of the respective weighted computations; for each of the plurality of monochromatic CT images, segmenting a surrounding region of a highly-absorbent material circumferentially into a plurality of regions of interest having a predetermined area and calculating a standard deviation of the surrounding region by using a mean value of image data of each of the regions of interest, and selecting a monochromatic CT image with a small standard deviation.

The plurality of weighted computations applied to the first energy level CT image and the second energy level CT image may be weighted summations.

The surrounding region of the highly-absorbent material may be determined based on a region that is affected by a highly-absorbent material artifact in the plurality of CT images acquired by irradiation of the radiation.

The surrounding region of the highly-absorbent material may be a region surrounding a region that is estimated to have a highly-absorbent material artifact therein, from which an adjacent region is removed, in the plurality of CT images acquired by irradiation of the radiation.

In accordance with another aspect, the disclosure provides a monochromatic CT image creating apparatus that applies computation processing to a plurality of CT images formed by irradiation of radiation of a plurality of energy levels. The apparatus acquires a first energy level CT image formed by irradiation of radiation of a first energy level and a second energy level CT image formed by irradiation of radiation of a second energy level; applies a plurality of weighted computations to the first energy level CT image and the second energy level CT image that are acquired, to compute a plurality of monochromatic CT images as a result of the respective weighted computations, and for each of the plurality of monochromatic CT images, segments a surrounding region of a highly-absorbent material circumferentially into a plurality of regions of interest having a predetermined area and calculates a standard deviation of the surrounding region by using a mean value of image data of each of the regions of interest, and selects a monochromatic CT image with a small standard deviation.

In accordance with another aspect, the disclosure provides a storage medium for storing a monochromatic CT image creation program for applying computation processing to a plurality of CT images formed by irradiation of radiation at a plurality of energy levels. The monochromatic image creation program causes a computer to: acquire a first energy level CT image formed by irradiation of radiation of a first energy level and a second energy level CT image formed by irradiation of radiation of a second energy level; apply a plurality of weighted computations to the first energy level CT image and the second energy level CT image that are acquired, to compute a plurality of monochromatic CT images as a result of the respective weighted computations, and segment a surrounding region of a highly-absorbent material circumferentially into a plurality of regions of interest having a predetermined area and calculate a standard deviation of the surrounding region by using a mean value of image data of each of the regions of interest, for each of the plurality of monochromatic CT images, and select a monochromatic CT image with a small standard deviation.

According to the disclosure, it is possible to determine an appropriate weight in a short time and to efficiently acquire a monochromatic CT image with highly-absorbent material artifacts being eliminated.

DESCRIPTION OF EMBODIMENTS

Embodiments of the disclosure will be described below by reference to the drawings. The present disclosure is not limited to the embodiments described below.

Figure 1:
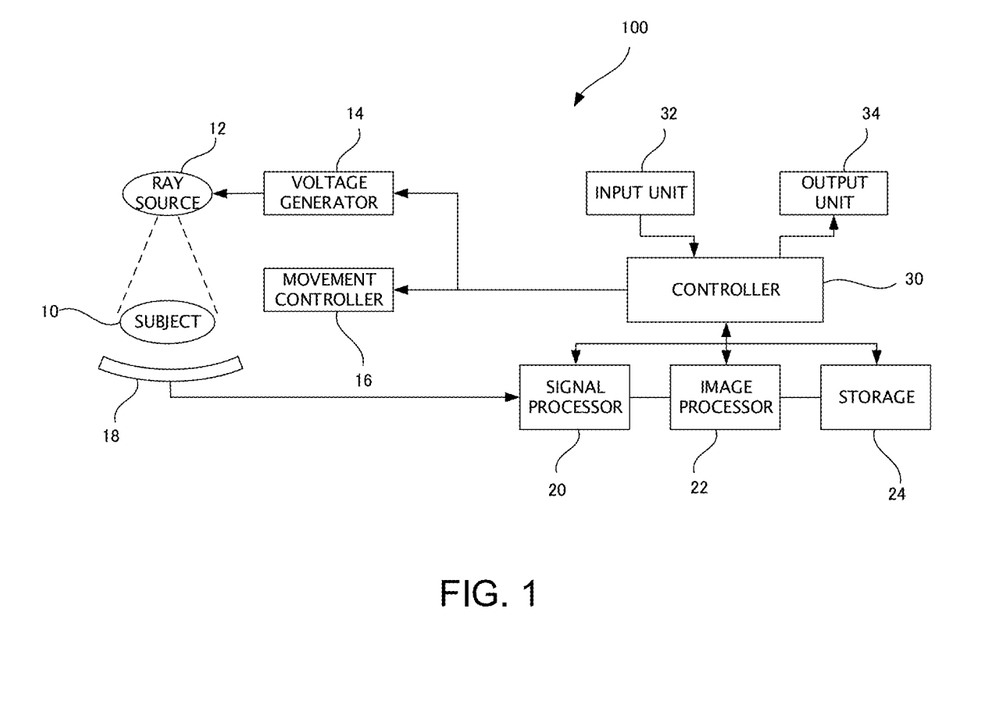
FIG. 1 is a block diagram illustrating an overall configuration of a CT apparatus 100 including a CT image creation device according to the present embodiment.

FIG. 1 is a block diagram illustrating an overall configuration of a CT apparatus 100 including a CT image creation apparatus according to an embodiment.

A subject 10 such as a patient to be diagnosed or treated is secured to an examining table (not shown), for example. A ray source 12 is disposed above the subject 10. The ray source 12 irradiates the subject 10 with radiation, and is an X-ray tube, in this example. The ray source 12 may generate high energy electromagnetic waves such as y-rays, rather than X-rays.

The ray source 12 is coupled to a voltage generator 14, which generates and supplies to the ray source 12 high voltage that is necessary for generating radiation in the ray source 12. In this example, the voltage supplied from the voltage generator 14 changes the tube voltage of an X-ray tube of the ray source 12, to thereby change the energy level of the X-ray to be emitted. To obtain a tomographic image of a predetermined range of the subject 10, the examining table for securing the subject 10 and the ray source 12 are allowed to move (rotate and axially translate). A movement controller 16 controls these movements.

A detector 18 is disposed below the subject 10 (on the side of the subject 10 further away from the ray source 12) to receive incident radiation transmitted through the subject 10, thereby obtaining a transmission image of the subject 10 as an electrical signal for each pixel.

The detector 18 is connected to a signal processor 20 that sequentially generates captured two-dimensional image data based on the electrical signals supplied from the detector 18. Specifically, the ray source 12 and the detector 18 rotate about the subject 10 to acquire image data from 360° directions. The acquired image data is supplied to an image processor 22, where the image data is subjected to various processing to form sequentially changing three-dimensional data which is to be stored in a storage 24. Based on the data stored in the storage 24, a desired CT image can be obtained.

According to the present embodiment, concerning a single CT image to be observed, captured CT images at two tube voltages (a first energy level and a second energy level) are selected and weighted-summated to create monochromatic CT images. In particular, a plurality of monochromatic CT images are created with the weight being changed, and an appropriate monochromatic CT image is selected as described below from among the plurality of monochromatic CT images. These processes may be performed by the image processor 22 using the data stored in the storage 24. At least the image processor 22 is composed of a computer, which executes a monochromatic CT image creation processing program to acquire a captured CT image stored in the storage 24 and perform these computations.

The CT device 100 further includes a controller 30 to control the operation of the voltage generator 14, the movement controller 16, the signal processor 20, and the image processor 22, for example. The controller 30 is connected to an input unit 32 and an output unit 34. The input unit 32, which is composed of a keyboard or a touch panel, is used by an operator to input various information. The output unit 34, which is composed of a display or a printer, outputs a desired image or text data.

Creation of Monochromatic CT Image

The energy level of the radiation to be emitted from the ray source 12 is controlled by outputting a voltage from the voltage generator 14 in accordance with an instruction from the controller 30. In the present embodiment, an image of the subject 10 is captured while moving the subject 10 (moving in the direction of the rotation axis of the ray source 12 and the detector 18) with radiation at two energy levels (the first energy level and the second energy level). The two types of image capturing may be performed in succession while moving the subject 10, or may be performed such that, after completing image capturing with the first energy level, image capturing with the second energy level is performed while moving the subject 10 once again.

After completion of the image capturing with two energy levels, each captured image data is stored in the storage 24. Desired captured CT images can then be created based on these captured image data items. At this time, captured CT images identical target with different energy levels are created and stored in the storage 24.

Then, a single CT image is specified based on an instruction from the input unit 32, and the specified CT image and the corresponding CT image with a different energy level are read out from the storage 24 and weighted-summated in the image processor 22.

Processing of Surrounding Region of Highly-Absorbent Material Region (Metal Region)

Metal is a highly-absorbent material with respect to radiation, and generates highly-absorbent material artifacts (metal artifacts) around the metal. To remove the metal artifacts, weighted summation is applied to two CT images. At this time, the weight is selected using, as an evaluation value, a standard deviation which represents a degree of distribution of mean values of regions of interest ROI, formed by segmenting a region surrounding the metal into a plurality of regions, such that the standard deviation is minimized. The metal region is easily recognizable in a CT image.

Figure 2A:
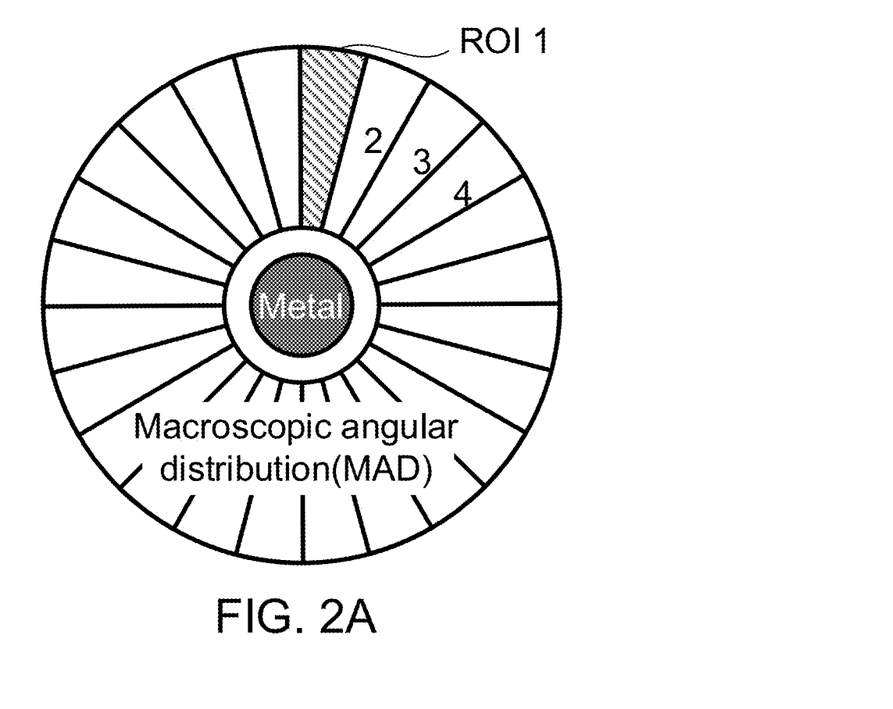
FIG. 2A illustrates a region of interest ROI around a metal region Metal.
Figure 2B:
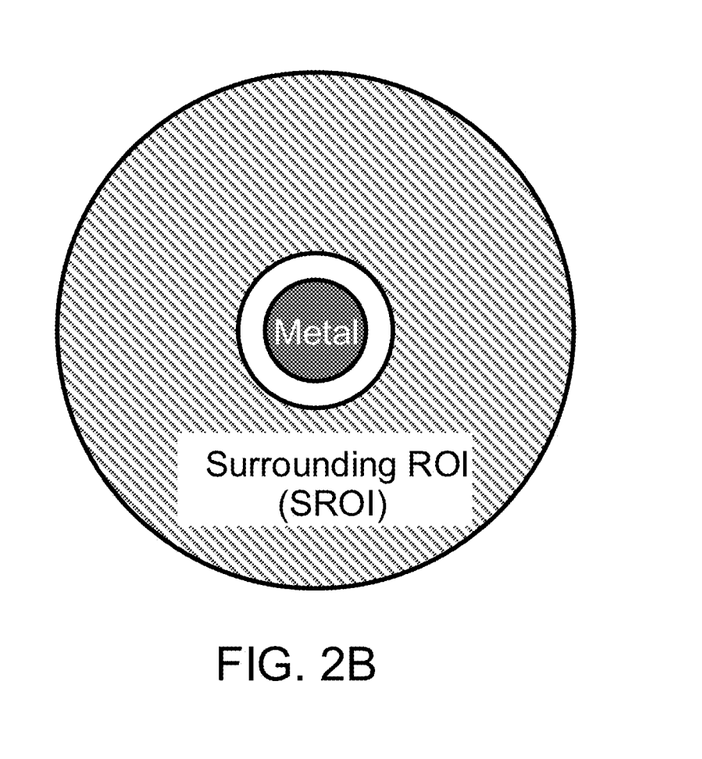
FIG. 2B illustrates a surrounding region of interest SROI around a metal region Metal.

FIG. 2A illustrates a metal region Metal and regions of interest ROI surrounding the metal region Metal, each having a sector shape. In this example, a surrounding region of interest SROI is segmented into twenty-four regions of interest ROI. Therefore, each region of interest ROI has a width of 15° in the circumferential direction about the center of the metal region Metal. FIG. 2B illustrates the metal region Metal and the surrounding region of interest SROI.

Weighted-Computation Using Standard Deviation

Figure 3:
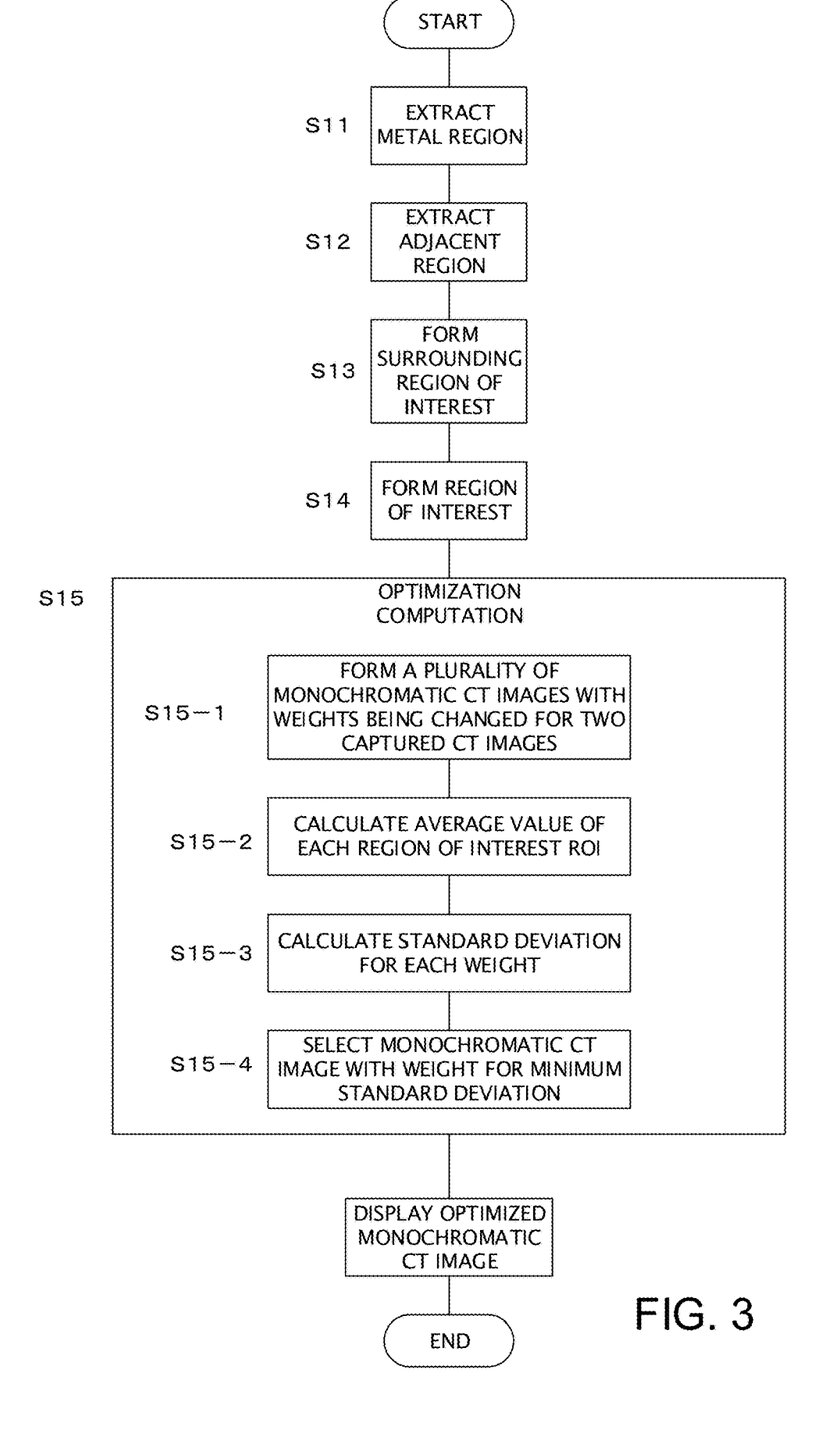
FIG. 3 is a flowchart illustrating a procedure for selecting an optimal monochromatic CT image.

FIG. 3 is a flowchart showing a procedure for selecting an optimal monochromatic CT image. First, the metal region Metal is extracted from a captured CT image (S11). This may be performed by detecting an edge based on a change in the CT value for each pixel in a single captured CT image. Here, the metal region Metal may be detected from among a plurality of CT images. When a single CT image is used for detecting the metal region Metal, an image with the highest energy level (tube voltage) may be used.

When the metal region Metal is extracted, an adjacent region corresponding to several pixels in the periphery of the metal region Metal is further extracted (S12), and a region outside the adjacent region is expanded outward to form a surrounding region of interest SROI (S13).

Here, the adjacent region may not necessarily be set. However, as a possibility that the metal region Metal may or may not be included in the surrounding region would increase an error in the standard deviation, it is appropriate to extract and remove the adjacent region from the surrounding region of interest SROI. As the adjacent region which is too large would reduce the region where metal artifacts are present and lower the evaluation accuracy, a region surrounding the metal region Metal that corresponds to several pixels in the radial direction may be set as the adjacent region. Alternatively, the surrounding region of interest SROI may be formed by expanding a region, from the metal region Metal, toward the peripheral outward region and then removing the adjacent region.

While the surrounding region of interest SROI can be a region corresponding to a region where the metal artifacts are present (region which is estimated to include the metal artifacts), the surrounding region of interest SROI may be slightly smaller or slightly larger than that region. If the metal region Metal has a diameter of about 1 cm, an annular region having a thickness of several cm surrounding the metal region Metal may be the surrounding region of interest SROI.

When the surrounding region of interest SROI is set as described above, this region is segmented in the circumferential direction into a plurality of equal sector-shape regions of interest ROI (S14). If the regions of interest ROI, which are segmented regions surrounding a single metal region Metal, are obtained, optimization computation processing for the weight is performed (S15).

In the optimization computation in step S15, for the selected two captured CT images, with the weight of one image being changed stepwise within a range of −9 to 10 while the weight of the other CT image being changed stepwise within a range of 10 to −9 such that the sum of these weights is always 1, monochromatic CT images are created by weighted-summing the two CT images with pairs of the respective weights (S15-1). For each of the obtained monochromatic CT images differently weighted, the mean value of image data (CT value) is calculated for each region of interest ROI (S15-2), and then the standard deviation of the mean values of the ROIs is calculated (S15-3). Then, a monochromatic CT image with the smallest standard deviation is selected (S15-4), and the selected monochromatic CT image is displayed on the output unit 34 (S16).

The present inventors performed verification using various captured CT images and confirmed that the monochromatic CT image with the smallest standard deviation that was selected according to such a weighted computation result is the optimal monochromatic CT image with the effects of the metal artifacts being removed.

As described above, according to the present embodiment, the monochromatic CT images obtained by a large number of different weighted summation computations are evaluated using the regions of interest ROI, so that an appropriate monochromatic CT image can be automatically determined.

EXAMPLES

FIGS. 4A to 4E show CT images obtained using Optima CT 580 W, which is a CT apparatus manufactured by General Electric Company, with GAMMEX phantom of SUN NUCLEAR employed as the subject 10.

Figure 4A:
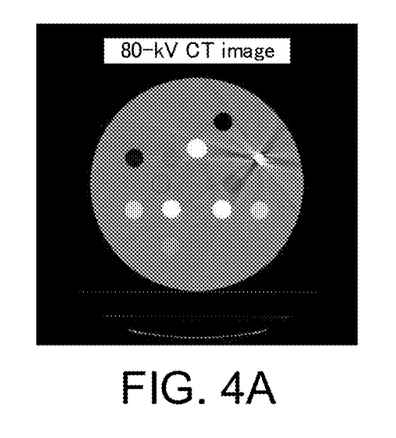
FIG. 4A is a captured CT image at tube voltage 80-kV.
Figure 4B:
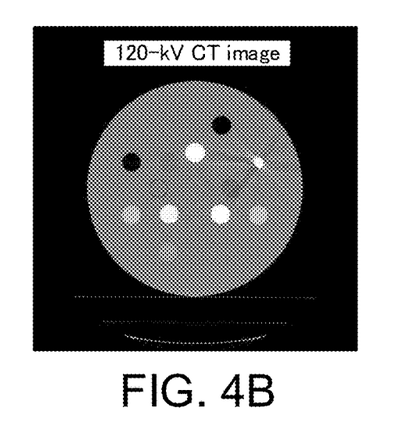
FIG. 4B is a captured CT image at tube voltage 110-kV.
Figure 4C:
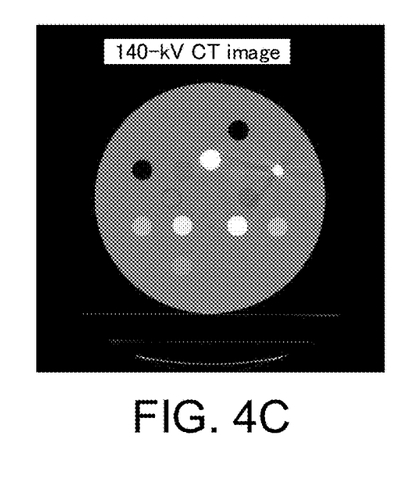
FIG. 4C is a captured CT image at tube voltage 140-kV.

FIG. 4A shows a captured CT image at the tube voltage of 80-kV, FIG. 4B shows a captured CT image at the tube voltage of 120-kV, and FIG. 4C shows a captured CT image at the tube voltage of 140-kV. The GAMMEX phantom includes a single titanium, as a metal, embedded therein. In FIGS. 4A to 4C, a circle which appears bright (that is, showing artifacts around it) corresponds to an image of the titanium. The GAMMEX phantom used as the subject 10 includes a base that imitates water, and inserts that imitate bones, for example, embedded in the base, and the inserts have lightness that is different from that of the base. In these images, the inserts with large absorption are shown in white.

Figure 4D:
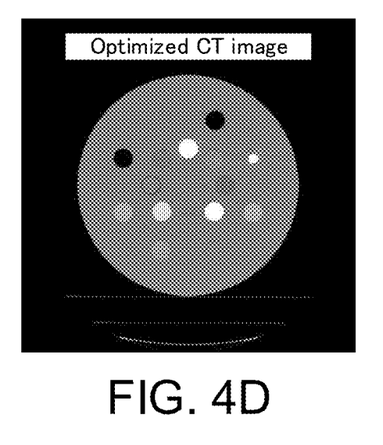
FIG. 4D is an optimized monochromatic CT image.

FIG. 4D shows an optimized monochromatic CT image which is determined by the optimization of the present embodiment, that is, determined, from among a plurality of monochromatic CT images obtained by weighted summation of the captured CT image of 80-kV (FIG. 4A) and the captured CT image of 140-kV (FIG. 4C), such that the standard deviation SDMAD of the mean values of the twenty-four regions of interest ROI illustrated in FIG. 2A is the smallest. Further, FIG. 4E shows an optimized monochromatic CT image obtained in a similar manner when the CT images to be processed include random white noise added thereto.

Figure 4E:
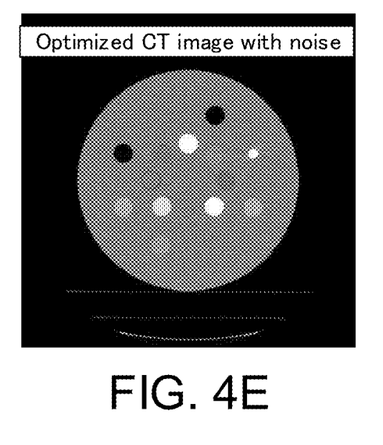
FIG. 4E is an optimized monochromatic CT image with white noise added.

The CT images shown in FIG. 4A to FIG. 4E have the following standard deviations SDMAD of the mean values of the regions of interest ROI: 93.588 in FIG. 4A; 35.357 in FIG. 4B; 26.579 in FIG. 4C; 7.343 in FIG. 4D; and 7.597 in FIG. 4E. Further, the CT images shown in FIG. 4A to FIG. 4E have the following standard deviations SDSROI of the surrounding regions of interest SROI: 128.286 in FIG. 4A; 50.363 in FIG. 4B; 37.643 in FIG. 4C; 18.687 in FIG. 4D; and 30.961 in FIG. 4E.

As described above, a captured CT image formed with higher tube voltage has smaller standard deviations SDMAD and SDSROI. Further, it is understood from the monochromatic CT image in FIG. 4D with the minimum standard deviation SDMAD according to the method of the present embodiment, that the standard deviation SDSROI is also sufficiently smaller than that of the captured CT image and the metal artifacts are removed.

Concerning the standard deviations SDMAD and SDROI of the optimized CT image with white noise illustrated in FIG. 4E, while the standard deviation SDSROI increases by about 65% due to effects of white noise, the standard deviation SDMAD rises by only 3 to 4%. This indicates that the standard deviation SDMAD, for use in the present embodiment, that is obtained based on the mean values of the regions of interest ROI, is less affected by white noise and therefore enables appropriate calculation of a weight even with the presence of white noise. In other words, it is possible to select an image with metal artifacts being removed, by selecting a monochromatic CT image with the minimum standard deviation SDMAD, regardless of the effect of white noise.

According to the present embodiment, as described above, it is possible to automatically obtain a monochromatic CT image with the effect of metal artifacts being reduced, by selecting appropriate weighted summation computation for two captured CT images. This process requires about 3 seconds, which is about 5 times shorter than the conventional technique which requires manual selection of an optimal image and requires about 15 seconds. The method according to the present embodiment can further shorten the required time when a high performance computer is employed, so that the operator can see the appropriate monochromatic CT image immediately without substantially no waiting.

According to the present embodiment, in radiation diagnosis and treatment, an image with the minimized metal artifact effect is automatically presented. This is considered to be particularly effective for adaptive radiation treatment (ART: Adaptive Radiotherapy, Immediate Adaptive Radiation Treatment). More specifically, even when radiation cannot be emitted as originally planned due to a change in the body shape or a change in the size of a lesion, and a change in the position of an organ, for example, during treatment, an appropriate CT image which can be obtained immediately at the time of treatment can be used for rescheduling in the middle of the treatment such that more appropriate treatment can be maintained.

Segmentation of Region of Interest

While in the above example the metal region Metal has a circular shape, metal is not limited to a circular shape. In such a case, a region surrounding the metal region may be extended by a certain distance in the direction vertical to a tangential line of the metal region to thereby determine a surrounding region of interest SROI along the periphery of the metal region, for example, and the regions of interest ROI may then be obtained by segmenting the determined surrounding region of interest SROI. For example, the area of the surrounding region of interest SROI is divided by a desired number to obtain an ROI area, so that individual regions of interest ROI may be set for each ROI area determined from a predetermined reference position (radial line).

Figure 5:
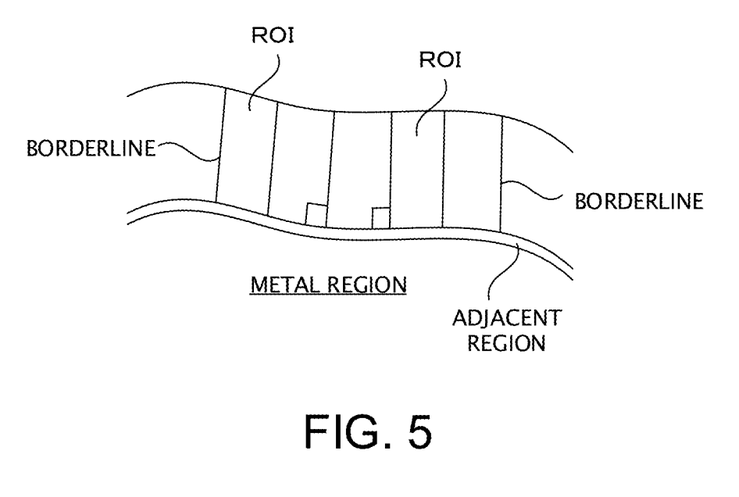
FIG. 5 illustrates another example region of interest ROI.

In this case, it is possible to expand the width (central angle) of a surrounding region using the center of gravity of the metal region Metal as a reference to determine the region of interest ROI for each determined ROI area. Further, as illustrated in FIG. 5, one borderline may be determined in a direction at a normal angle with respect to the peripheral edge of the metal and the other borderline may be determined for each ROI area.

Optimization Computation

In the above example, in the weighted computation, the weight is divided at predetermined intervals and optimization is performed by calculating the standard deviations SDMAD based on the mean values of the respective regions of interest ROI, for selecting a weighted monochromatic CT image with the minimum standard deviation SDMAD. However, the optimization computation is not limited to a one-time computation; a computation method in which the interval for dividing the weight is sequentially reduced may be adopted. For example, a method in which two weights resulting in the two minimum standard deviations are selected and the interval between the two weights is further divided to thereby determine the weight for the minimum standard deviation may be adopted. Further, weighted multiplication, rather than weighted summation, may be adopted.

Standard Deviation

While in the above example the "standard deviation" is used as an evaluation value, distribution may be employed, as the same result can be obtained when distribution is used as an evaluation value with the minimum variation.

Application Field

Creation of a CT image according to the present embodiment may be employed not only in the medical field but also in various fields including material analysis, for example.

Subject of Weighted Computation

In the above example, two captured CT images are used for weighted computation. However, optimization computation may be performed for three or more captured CT images while modifying combinations of weights to determine the optimal weight combination, thereby obtaining a monochromatic CT image. Alternatively, optimization computation may be performed for each of a plurality of combinations of two of three or more captured CT images, and an optimized monochromatic CT image with the minimum standard deviation may be selected from among the obtained optimal monochromatic CT images.

The invention claimed is:

1. A method for creating a monochromatic CT image by applying computation processing to a plurality of CT images formed by irradiation of radiation at a plurality of energy levels, the method comprising:
    acquiring a first energy level CT image by irradiation of radiation of a first energy level;
    acquiring a second energy level CT image by irradiation of radiation of a second energy level;
    applying a plurality of weighted computations to the first energy level CT image and the second energy level CT image that are acquired, to obtain a plurality of monochromatic CT images as a result of the respective weighted computations, and
    for each of the plurality of monochromatic CT images, segmenting a surrounding region of a highly-absorbent material circumferentially into a plurality of regions of interest having a predetermined area and calculating a standard deviation of the surrounding region by using a mean value of image data of each of the regions of interest, and selecting a monochromatic CT image with a small standard deviation.

2. The method for creating a monochromatic CT image according to claim 1, wherein
    the plurality of weighted computations applied to the first energy level CT image and the second energy level CT image are weighted summations.

3. The method for creating a monochromatic CT image according to claim 2, wherein
    the surrounding region of the highly-absorbent material is determined based on a region that is affected by highly-absorbent material artifacts in the plurality of CT images acquired by irradiation of the radiation.

4. The method for creating a monochromatic CT image according to claim 2, wherein
    the surrounding region of the highly-absorbent material is a region surrounding a region that is estimated to have highly-absorbent material artifacts therein, from which an adjacent region is removed, in the plurality of CT images acquired by irradiation of the radiation.

5. The method for creating a monochromatic CT image according to claim 1, wherein
    the surrounding region of the highly-absorbent material is determined based on a region that is affected by highly-absorbent material artifacts in the plurality of CT images acquired by irradiation of the radiation.

6. The method for creating a monochromatic CT image according to claim 1, wherein
    the surrounding region of the highly-absorbent material is a region surrounding a region that is estimated to have highly-absorbent material artifacts therein, from which an adjacent region is removed, in the plurality of CT images acquired by irradiation of the radiation.

7. A monochromatic CT image creating apparatus that applies computation processing to a plurality of CT images formed by irradiation of radiation of a plurality of energy levels, wherein the apparatus:

acquires a first energy level CT image formed by irradiation of radiation of a first energy level and a second energy level CT image formed by irradiation of radiation of a second energy level;

applies a plurality of weighted computations to the first energy level CT image and the second energy level CT image that are acquired, to compute a plurality of monochromatic CT images as a result of the respective weighted computations; and for each of the plurality of monochromatic CT images, segments a surrounding region of a highly-absorbent material circumferentially into a plurality of regions of interest having a predetermined area and calculates a standard deviation of the surrounding region by using a mean value of image data of each of the regions of interest, and selects a monochromatic CT image with a small standard deviation.

8. A non-transitory storage medium for storing a monochromatic CT image creation program for applying computation processing to a plurality of CT images formed by irradiation of radiation at a plurality of energy levels, the monochromatic image creation program causing a computer to:

acquire a first energy level CT image formed by irradiation of radiation of a first energy level and a second energy level CT image formed by irradiation of radiation of a second energy level;

apply a plurality of weighted computations to the first energy level CT image and the second energy level CT image that are acquired, to compute a plurality of monochromatic CT images as a result of the respective weighted computations; and segment a surrounding region of a highly-absorbent material circumferentially into a plurality of regions of interest having a predetermined area and calculate a standard deviation of the surrounding region by using a mean value of image data of each of the regions of interest, for each of the plurality of monochromatic CT images, and select a monochromatic CT image with a small standard deviation.

* * * * *